United States Patent [19]

Pruckmayr

[11] Patent Number: 4,584,414

[45] Date of Patent: Apr. 22, 1986

[54] PROCESS FOR PREPARING IMPROVED POLY(TETRAMETHYLENE ETHER) GLYCOL BY ALCOHOLYSIS

[75] Inventor: Gerfried Pruckmayr, Media, Pa.

[73] Assignee: E. I. Du Pont de Nemours and Company, Wilmington, Del.

[21] Appl. No.: 685,017

[22] Filed: Dec. 21, 1984

[51] Int. Cl.$^4$ .............................................. C07C 41/18
[52] U.S. Cl. .................................................. 568/617
[58] Field of Search ........................................ 568/617

[56] References Cited

U.S. PATENT DOCUMENTS 4,230,892 10/1980 Pruckmayr ........................... 568/617
4,460,796 7/1984 Mueller ................................. 568/617

Primary Examiner—Howard T. Mars

[57] ABSTRACT

In the process of converting a poly(tetramethylene ether) diester to poly(tetramethylene ether) glycol by catalytic alcoholysis, using an alkali metal hydroxide or alkoxide as the catalyst, contamination of the polymer product can be reduced by reacting the catalyst with an acid after the alcoholysis reaction is complete, and then removing the reaction product from the reaction mass.

1 Claim, No Drawings

PROCESS FOR PREPARING IMPROVED POLY(TETRAMETHYLENE ETHER) GLYCOL BY ALCOHOLYSIS

DESCRIPTION

1. Technical Field

This invention relates to a method for preparing poly(tetramethylene ether) glycol (PTMEG). It is more particularly directed to a method for preparing PTMEG from poly(tetramethylene ether) diester by alcoholysis.

2. Background and Summary of the Invention

PTMEG is a commodity in the chemical industry, widely used in the preparation of polyesters and polyurethanes. A variety of methods is known for manufacturing PTMEG, one being that shown in U.S. Pat. No. 4,163,115.

In that method, tetrahydrofuran is polymerized in a medium which contains acetic anhydride. This leads to a poly(tetramethylene ether) diester, which must then be converted to PTMEG. That conversion can be made by catalytic alcoholysis, using as the catalyst an alkali metal hydroxide or methoxide. This method of conversion has the advantage of being fast, but leaves catalyst residue in the polymer product, which may cause discoloration and which may lead to reactivity problems in subsequent chain extension processes.

I have now found that the amount of catalyst residue can be significantly reduced if, after the alcoholysis reaction, the catalyst is reacted with an acid and the catalyst-acid reaction product is then removed from the reaction medium.

DETAILED DESCRIPTION OF THE INVENTION

A mixture of poly(tetramethylene ether) diester starting material, catalyst and an alkanol is first prepared. This may be done by simply bringing the components together in a reactor. Preferably, the catalyst is first slurried in the alkanol and this slurry then mixed with a solution of the diester in the alkanol.

The diester starting material will ordinarily be a diacetate produced as shown in U.S. Pat. No. 4,163,115, although other diesters such as the propionates and butyrates can be used.

The catalyst used may be any alkali metal hydroxide or alkoxide. Sodium hydroxide is preferred.

The alkanol used may be one containing 1-4 carbon atoms, and will preferably be methanol.

The mixture is prepared so that it contains
(a) diester, 5-80% by weight, preferably 20-60%;
(b) alkanol, 20-95% by weight, preferably 40-80%; and
(c) catalyst, about 1-25 mol percent based on the diester, preferably 8-20 mol percent.

The pH of the mixture should be 8 or higher.

The reaction mixture is brought to its boiling point and held there, with stirring, while vapors of the alkanol-alkyl ester azeotrope are continuously withdrawn from the reaction zone. In the usual case, the boiling point of the mixture will be in the range of about 50°-150° C. This boiling and withdrawal of azeotrope is continued until alcoholysis is substantially complete, i.e., until no more alkyl ester is detected in the distillate being removed, as determined by gas chromatography.

At this point, a slight excess over the stoichiometric amount of an acid is added to the reaction mass, with stirring. This acid can be any that is volatile at the reaction temperature and which forms a catalyst-acid reaction product that is insoluble in the reaction mass ("insoluble" meaning that substantially all of it can be removed from the mass by filtration, only insignificant amounts remaining). Monocarboxylic acids of 1-4 carbon atoms are preferred; acetic acid is most preferred.

The mass is then brought to a temperature of 100°-150° C. and a pressure of less than 50 mm of Hg to remove unreacted alkanol and acid. The product is then filtered to remove the solid catalyst-acid reaction product.

The resulting PTMEG product may contain as little as 2 ppm of alkali metal, as determined by atomic absorption.

EXAMPLE

Those skilled in this art will be able to practice this invention more easily after referring to the following illustrative example.

These artisans will no doubt be able to compose numerous variations on the theme disclosed, such as changing the amounts of components slightly but insignificantly from those shown, adding innocuous substances, or substituting equivalent or nearly equivalent components for those shown. All these variations are considered to be part of the inventive concept.

In the Example, all parts are by weight.

One hundred parts of the diacetate of PTMEG, number average molecular weight 1000, were dissolved in 100 parts of methanol containing 0.2 parts of NaOH.

The mixture was brought to a boil, with stirring, and the methyl acetate which formed was removed by distillation as the methanol azeotrope. Fresh methanol was fed into the system at the same rate it was removed. Progress of the reaction was monitored by gas chromatography.

After 90 minutes, there was no longer a detectable peak of methyl acetate in the gas chromatogram of the distillate. At this point, 0.4 parts of acetic acid were added. The product was then dried under vacuum (less than 1 mm of Hg) at 120° C. for two hours. The product, PTMEG of number average molecular weight 1000, had an acid number of 0.0 and contained less than 1 ppm of Na.

I claim:

1. In a process for converting poly(tetramethylene ether) diester to poly(tetramethylene ether) glycol (PTMEG) by catalytic alcoholysis using an alkali metal hydroxide or alkoxide as the catalyst, the improvement comprising a method for reducing contamination of the PTMEG with catalyst residue which comprises reacting the catalyst, after the alcoholysis reaction is substantially complete, with an excess of acetic acid which forms a catalyst-acid reaction product that is insoluble in the reaction mass, and then vaporizing the excess acid and separating the catalyst-acid reaction product from the reaction mass.

* * * * *